United States Patent [19]

Deschler et al.

[11] Patent Number: 4,999,249

[45] Date of Patent: Mar. 12, 1991

[54] MIXTURES CONTAINING ORGANOSILICON COMPOUNDS AND THEIR USE FOR WATERPROOFING AND ANTIMICROBIAL IMPREGNATION

[75] Inventors: Ulrich Deschler, Hanau; Ulrike Lechner, Offenbach; Michael Witzel, Frankfurt, all of Fed. Rep. of Germany

[73] Assignee: Degussa Aktiengesellschaft, Frankfurt, Fed. Rep. of Germany

[21] Appl. No.: 399,586

[22] Filed: Aug. 28, 1989

[30] Foreign Application Priority Data

Feb. 25, 1989 [DE] Fed. Rep. of Germany ....... 3905919

[51] Int. Cl.$^5$ .............................................. B32B 9/04
[52] U.S. Cl. .................................... 428/447; 428/540; 106/2; 106/287.13
[58] Field of Search ................. 427/387, 393.6; 106/2, 106/287.13; 428/540, 447

[56] References Cited

U.S. PATENT DOCUMENTS 4,781,950 11/1988 Giesing et al. ...................... 427/421
4,877,654 10/1989 Wilson ............................... 106/2 X Primary Examiner—Michael Lusignan
Attorney, Agent, or Firm—Cushman, Darby & Cushman

[57] ABSTRACT

Mixtures containing organosilicon compounds and their use for the waterproofing and antimicrobial impreganation of stone, masonry and concrete. The organosilicon compounds are alkyltrialkoxy silanes and cationic trialkoxy silanes.

11 Claims, No Drawings

MIXTURES CONTAINING ORGANOSILICON COMPOUNDS AND THEIR USE FOR WATERPROOFING AND ANTIMICROBIAL IMPREGNATION

The present invention relates to mixtures containing organosilicon compounds and their use for waterproofing and antimicrobial impregnation.

BACKGROUND OF THE INVENTION

The use of alkyltrialkoxy silanes for waterproofing of masonry has long been known (see for example German Patent DE-PS 20 29 466 and published European Patent Application EP-A-0101 816).

Published European Patent Application EP-A-152 852 suggests the use of mixtures containing e.g. 2-methyl-1,4naphthoquinone, ethanol and propyltrimethoxy silane for the antimicrobial treatment of construction materials as well as the treatment of textiles or leather.

Published German Application DE-OS 3 031 598 (cf. U.S. Pat. Nos. 4,377,608, 4,377,675, 4,400,326, 4,404,196 and 4,404,306) teaches that metallic amine siliconates which exhibit antimicrobial properties, in a dry, amorphous form, can be worked into impregnating or coating materials such as e.g. alkyl resins. Published Japanese Application JP-OS 59/80 602 (C.A. 101 (15);124890 p, 1984) describes a mixture of triethoxymethyl silane and thiabendazole in toluene which is intended to limit the growth of mold on masonry surfaces.

SUMMARY OF THE INVENTION

The object of the present invention is to provide a way to simultaneously waterproof and protect inorganic, oxidic materials from microbial attack.

To achieve these objects, the present invention provides mixtures containing organosilicon compounds which contain:
(a) At least one alkyltrialkoxy silane of the general formula $$(RO)_3Si-R^1 \quad (I)$$

in which:
R represents $C_1-C_4$-alkyl, especially $C_1-C_2$-alkyl and
$R^1$ represents $C_1-C_{18}$-alkyl, especially $C_3-C_{18}$-alkyl,
(b) A cationic trialkoxy silane of the general formula

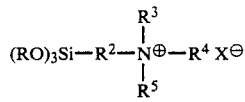

(II)

in which
$R^2$ represents $C_1-C_3$-alkylene,  $-CH_2-CH_2-CH_2-$
$R^3$, $R^4$, $R^5$, which may be the same or different from each other, represent $C_1-C_{18}$-alkyl
X represents $Cl^-$, $Br^{31}$, $NO_3^-$, Ihu —, $CH_3COO-$, and/or an organosilicon compound of the general formula $$(RO)_3Si-R^2-S-SnR^6{}_3 \quad (III)$$

in which
$R^6$ represents $C_1-C_6$-alkyl, especially n-butyl, or aryl, especially phenyl, in dissolved form or optionally emulsified in (c) A protic or aprotic solvent or solvent mixture.

Suitable solvents are alcohols, especially alkanols with 1 to 3 carbon atoms, but also alkanes with 5 to 30 carbon atoms and their mixtures like those obtainable e.g. as Shellsol on the market.

Aromatic hydrocarbons are also suitable solvents, but are not as desirable, because of environmental concerns. Water is also useful, especially in mixtures with alcohol(s), in which instance the ratio of water to alcohol is preferably set in accordance with the type of compounds selected for components (a) and (b) so that a solution is produced.

It is especially advantageous in these instances to use cationic organosilicon compounds such as those obtained in the form of aqueous solutions according the disclosure of European Patent EP-B-0 054 748.

The tin-bearing compounds described above are known from Izv. Sib. Otd. Akad. Nauk. SSR., Ser. Khim. Nauk; 1977 (1) pp. 128-134 (C.A. 86 (25): 190126 s (1977)).

The mixtures optionally may also contain compounds in which the compounds named under (a) and (b) are chemically bonded together. For convenience, these will be referred to as fusion products. For example, the oligomers created by splitting off partial amounts of the alcohol are known to persons skilled in the art, as is the mechanism of oligomer formation. Their presence has no adverse affect on the usefulness of the compositions according to the present invention.

The mixtures of the invention contain 5 to 97 % by weight, especially 10 to 40 % by weight, alkyltrialkoxy silane(s) (I) and their optionally present fusion products, 2 to 20 % by weight, especially 5-15 % by weight, compounds according to formulas (II) and/or (III) and their optionally present fusion products and 1 to 93 % by weight, especially 55 to 85 % by weight, solvent.

In addition to these compounds, the mixtures advantageously may contain 0.1 to 5.0 % by weight, especially 0.1 to 1.0 % by weight, of a known condensation catalyst such as e.g. dibutyl tin dilaurate or tetrabutyl titanate. Compounds of the general formulas:

(IV)

and

(V)

in which n=8 to 18 are used with preference as cationic trialkoxy silanes.

Compounds of this type possess antimicrobial activity. 3-(trimethoxysilyl)propyldimethyloctadecyl ammonium chloride is used, e.g. in polyurethane foams, on account of this property (J. Cell. Plast. 21(5) 332-7 (C.A. 105 (2): 7525v, (1985)).

The present invention also provides a method of impregnating inorganic, oxidic material with the mixtures of the invention to render them waterproofing and for antimicrobial protection.

The inorganic oxidic materials which can be impregnated include, in particular, stone, masonry, concrete and external facade plaster such as stucco.

The mixtures may be applied to the surfaces in a generally known manner, e.g. by immersion, brushing, painting, spraying or a flooding treatment with the mixture. In general, as much of the composition is applied as the oxidic material can absorb. This is generally recognized in that the silane to be applied does not remain visible on the surface longer than approximately one minute, that is, the surface appears moist to a saturated extent only briefly. The surface to be treated can be either dry or moist with water. However, there should not be any standing water on it. The only important condition is that the surface can absorb the mixture; it must therefore not be so soiled e.g. by dust, salt, saline solution or oil that the absorption action is reduced to any considerable extent. Surfaces soiled to this extent may be cleaned in a known manner prior to the application.

In this manner, an inorganic, oxidic material can be waterproofed, and, at the same time, antimicrobial properties are imparted to it. The treatment provides not only a surface treatment, but there is also a deep action. The addition of the cationic organosilicon compounds has the surprising effect, in spite of its small amount, that the penetration depth of the waterproofing agent is increased and, at the same time, the risk of water penetrating into and being absorbed by the inorganic oxidic material is reduced.

This is also surprisingly true for cationic compounds which carry an $R^4$ substituent which is a $-C_{18}-H_{37}$ group, from which compounds the opposite would have been expected as regards the penetration depth.

It can be determined at the same time that the cationic compounds according to general formula (II), functioning as solublizer, raise the solubility of alkyltrialkoxy silanes in the water/alcohol mixture.

DETAILED DESCRIPTION OF PREFERRED EMBODIMENTS

The invention will be illustrated with a series of tests which demonstrate the action of the mixtures of the invention.

Test procedure:

Stone specimens (5×5×5 cm; material: lime sandstone) are first conditioned for a few weeks in a normal climate (23° C., 50 % rel. moisture) and subsequently weighed. 200 ml of the silane mixture are placed in a 400 ml beaker and three specimens at a time are completely immersed for 2 min. twice at an interval of one half an hour. After the silanizing has taken place, the stone blocks are stored 14 days at room temperature. In order to determine the water absorption, two specimens at a time are placed into a water bath with 5 cm supernatant water column and the weight is monitored after 10 min., 30 min., 60 min., 2 hours, 4 hours, 8 hours and 24 hours (Temperature : 20.C). In order to measure the penetration depth, the specimen cubes are fractured with a hammer and chisel and sprayed with water dyed with ink. The following compounds are used:

Si 103: propyltrimethoxy silane
Si 108: n-octyltrimethoxy silane
Si 118: n-octadecyltrimethoxy silane
Si 275: 3-(triethoxysilyl) propyldimethyloctadecyl ammonium chloride.

Isopropanol is used as solvent and n-butyl titanate as catalyst. The concentration data corresponds to % by weight relative to the total amount of the mixture, as in the other parts of this disclosure.

| Silane mixture | Weight increase in % water bath (24 h) | Penetration depth of silane (mm) |
| --- | --- | --- |
| Control (untreated) | 10.27 | — |
| Si 103: 10% | 6.11 | 1.5–2.5 |
| Si 103: 10%, Si 275: 5% | 1.01 | 2–4 |
| Si 103: 10%, Si 275: 5% Catalyst 0.5% | 0.92 | 2–4 |
| Si 108: 10% | | 3–4 |
| Si 108: 10%, Si 275: 5% | 0.79 | 3–6 |
| Si 108: 10%, Si 275: 5% Catalyst 0.5% | 0.91 | 3–6 |
| Si 118: 10% | 3.68 | 1–2 |
| Si 118: 10%, Si 275: 5% | 0.85 | 1.5–2.5 |
| Si 118: 10%, Si 275: 5% Catalyst 0.5% | 0.77 | 1–2 |

What is claimed is:

1. A composition for the treatment of inorganic, oxidic material comprising waterproofing and antimicrobial effective amounts of:
   (a) $(RO)_3Si-R^1$ (I) in which:
   R represents $C_1-C_4$-alkyl
   $R^1$ represents $C_1-C_{18}$-alkyl
   (b) A cationic trialkoxy silane of the general formula

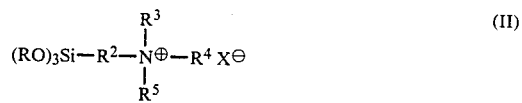

in which:
   $R^2$ represents $C_1-C_3$-alkylene or $-CH^2-CH^2-CH_2-$
   $R^3$, $R^4$, $R^5$, which may be the same or different from each other, represent $C_1-C_{18}$-alkyl
   X represents $Cl^-$, $Br^-$, $NO_3^-$, $I^-$, $CH_3COO^-$, and/or an organosilicon compound of the general formula

in which
   $R^6$ represents $C_1-C_6$-alkyl or aryl or fusion products of (a) and/or (b).

2. A composition according to claim 1 which contains a fusion product of an organosilicon compounds (a) or (b).

3. A composition according to claim 1 in which R is $C_1-C_2$-alkyl,
   $R^1$ represents $C_3-C_{18}$-alkyl, $R^6$ represents n-butyl or phenyl.

4. A composition according to any one of claims 1, 2 or 3 in which the components (a) and (b) are dissolved or emulsified in a protic or aprotic solvent.

5. A composition according to claim 4 which contain 5 to 97 % by weight alkyltrialkoxy silane(s) o their fusion products, 2–20 % by weight compounds according to formulas (II) and/or (III) or their fusion products and 1 to 93 % by weight protic or aprotic solvent.

6. A composition according to claim 4 which also contains 0.1 to 5.0 % by weight of a condensation catalyst for said components (a) and or (b).

7. A composition according to claim 4 which contains a cationic trialkoxy silane of the general formula

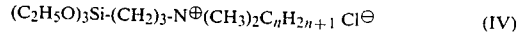

or $$(C_2H_5O)_3Si\text{-}(CH_2)_3\text{-}N^{\oplus}(CH_3)(C_nH_{2n+1})_2Cl^{\ominus} \qquad (V)$$

with $n = 8$ to $18$.

8. A method for the waterproofing and imparting antimicrobial characteristics to an inorganic, oxidic material which comprises applying thereto a composition according to claim 4.

9. A method as set forth in claim 8 in which the inorganic, oxidic material is selected from the group consisting of sandstone, masonry, concrete or external facade plaster.

10. An inorganic, oxidic material which has been treated by the method of claim 8.

11. An inorganic, oxidic material as set forth in claim 10 in which the inorganic, oxidic material is selected from the group consisting of sandstone, masonry, concrete or external facade plaster.

* * * * *